United States Patent [19]

Stetter et al.

[11] Patent Number: 5,512,882
[45] Date of Patent: Apr. 30, 1996

[54] CHEMICAL SENSING APPARATUS AND METHODS

[75] Inventors: Joseph R. Stetter, Naperville; G. Jordan Maclay, Maywood, both of Ill.

[73] Assignee: Transducer Research, Inc., Aurora, Ill.

[21] Appl. No.: 741,573

[22] Filed: Aug. 7, 1991

[51] Int. Cl.$^6$ .................................................. G08B 17/10
[52] U.S. Cl. ................................................ 340/632; 73/31.05
[58] Field of Search ................................... 340/632, 605, 340/691; 73/31.05, 23.21; 324/71.1, 610; 200/61.03; 338/34; 204/424–429; 436/151; 422/88, 98, 82.02, 58

[56] References Cited

U.S. PATENT DOCUMENTS

| | | | |
|---|---|---|---|
| 4,200,538 | 4/1980 | Seita et al. | 210/500.41 |
| 4,447,292 | 5/1984 | Schuster-Woldan et al. | 156/644 |
| 4,454,007 | 6/1984 | Pace | 204/153.1 |
| 4,572,900 | 2/1986 | Wohltjen | 73/23.21 X |
| 4,631,952 | 12/1986 | Donaghey | 73/31.05 X |
| 4,786,837 | 11/1988 | Kalnin et al. | 310/364 |
| 4,925,544 | 5/1990 | Goldring | 204/421 |
| 4,926,165 | 5/1990 | Lahlouh et al. | 340/605 X |
| 5,028,394 | 7/1991 | Lowell, Jr. et al. | 422/58 |
| 5,109,202 | 4/1992 | Akiba | 340/605 X |
| 5,145,645 | 9/1992 | Zakin et al. | 73/31.05 X |
| 5,150,603 | 9/1992 | Boenning et al. | 73/31.05 |
| 5,222,388 | 6/1993 | Sinha et al. | 73/31.05 X |

FOREIGN PATENT DOCUMENTS 15646 of 1989 Japan ................................ 340/605

*Primary Examiner*—Thomas Mullen
*Attorney, Agent, or Firm*—Solomon Zaromb

[57] ABSTRACT

Apparatus for the detection of a vapor of a selected chemical substance includes a sensor whose impedance changes upon exposure to such a vapor. The sensor comprises a polymer whose physical structure is altered by the vapor, e.g., through expansion or disintegration, and electrically conductive elements that are interspersed with or separated by the polymer. The interspersed elements may consist of a fine powder of carbon or of a metal in a matrix of silicone or other vapor-sensitive polymer. The electrical contacts between the powder particles are weakened when the polymer swells or disintegrates, which results in increased resistance. Alternatively, the capacitance between two conductive layers separated by a polymer layer decreases, and hence the impedance increases, when the polymer swells upon exposure to the vapor. In yet another embodiment, the polymer exerts a stress on a piezoresistive element and the stress is increased when the polymer swells, which causes a further increase in resistance. The changes are measured by an impedance-measuring circuit, such as a Wheatstone bridge.

26 Claims, 7 Drawing Sheets a = Dry
b = 370 ppm C$_6$H$_{12}$
c = 920 ppm C$_6$H$_{12}$ a = Dry
b = Humid Air ; c = 500 ppm C$_6$H$_{12}$ (Humidified)
d = 2200 ppm (Humidified)

a = Dry
b = Humid Air
c = 500 ppm $C_6H_{12}$ (Humidified)

CHEMICAL SENSING APPARATUS AND METHODS

BACKGROUND OF THE INVENTION

This invention relates to chemical sensors which detect the presence of selected air contaminants through changes in electrical impedance resulting from structural changes in a vapor-sensitive polymer. More specifically, the invention relates to sensors that can be incorporated in gas filtering devices so as to provide a warning when the life of a filter is at or near exhaustion.

Air purifying respirator cartridges are used to allow workers to remain in an ambient which contains toxic gases that would be harmful to breathe. Depending on the concentration of the toxic gas and other factors, a respirator cartridge may last from minutes to days before the adsorbent bed is expended. One of the major problems users face is determining when the service life has ended. It is an object of this invention to provide an active-end-of-service-life-indicator (AEOSLI) that could be placed in the adsorbent bed and would signal the user when the life of the cartridge was nearing the end.

The presence of an unambiguous signal warning the user that the cartridge is almost expended would give greater protection to the user, who would not have to rely on sensory indicators such as dizziness. In addition, an AEOSLI could be used for those toxic gases for which there is no sensory warning, regulations permitting. This could lead to the use of air-purifying respirators with many compounds which now require the use of a SCBA (self-contained breathing apparatus).

The development of an AEOSLI is of especially great significance today since the official threshold level values of about 500 compounds have been lowered, and adequate sensory warning is not provided at these reduced levels for many compounds. An AEOSLI will make it possible to continue to employ an air purifying respirator instead of a SCBA in many applications. Simple positive and negative pressure respirators provide the economic benefits of lower cost and increased productivity, as well as improved safety and comfort for workers. All in all, an AEOSLI offers the very important advantages of safer and more economical protection (no need to undergo sensory warning or change canisters for every shift) and of allowing the use of air-purifying respirators with compounds that don't provide sensory warning at the permissible levels. Thus, the AEOSLI could result in considerable savings to industry and in increased worker safety and comfort.

It is a major objective of this invention to provide an AEOSLI with an unambiguous alarm to warn the user when at least 10% of the respirator cartridge life remains without the AEOSLI interfering with the operation of the respirator.

It is another purpose of this invention to provide novel microchemical sensors that operate on very little power and can detect low levels of chemical vapors and gases inside an active adsorbent bed.

It is yet another object of the invention to interface the new microsensor technology with existing adsorbent-based protection systems to create a new respiratory protection device that can alert and alarm the user when the adsorbent is spent and the protection is not adequate.

It is still another object of the invention to provide small chemical sensors that are very low in cost and power consumption.

The prior art pertaining to AEOSLI devices includes U.S. Pat. No. 4,847,594, issued on Jul. 11, 1989, to J. R. Stetter, and U.S. Pat. No. 4,873,970, issued on Oct. 17, 1989, to M. Freidank et al. The patent to Freidank et al. utilizes electrochemical sensors only. Chemiresistive sensors are disclosed in Stetter's patent and also in James P. Dolan's U.S. Pat. No. 4,129,030 (Dec. 12, 1978), U.S. Pat. No. 4,224,595 (Sep. 23, 1980), and U.S. Pat. No. 4,237,721 (Dec. 9, 1980). However, none of these patents disclose chemiresistive sensors that are based on structural changes in vapor-sensitive polymers.

It is therefore still another object of the invention to provide chemical sensors in which the electrical impedance changes as a result of structural changes in a polymer upon exposure to certain vapors.

SUMMARY OF THE INVENTION

Briefly, the invention is based on structural changes that occur in certain polymers, especially elastomers, upon exposure to vapors of selected chemical substances, hereafter referred to as analytes. Some polymers disintegrate or swell when exposed to certain analyte vapors, and different analytes have different swelling or disintegrating effects on different polymers. It is thus possible to achieve selectivity towards different analytes through the choice of a proper polymer. It also becomes possible to design chemical sensors in which electrically conductive components are either intermingled with or supported by a polymer so that swelling or disintegration of the polymer upon exposure to an analyte vapor causes an increase in impedance between two or more of these elements. The conductive elements may consist of fine particles interspersed with a polymer, e.g., carbon powder mixed with silicone, or they may consist of two or more larger conductors bonded to an elastomer. In either case, a structural change in the polymer upon exposure to analyte vapor causes a change in impedance that can be measured by an electrical circuit, such as a Wheatstone bridge.

BRIEF DESCRIPTION OF THE DRAWINGS

The invention may be best explained with reference to the drawings in which.

DESCRIPTION OF THE PREFERRED EMBODIMENTS

Figure 1:
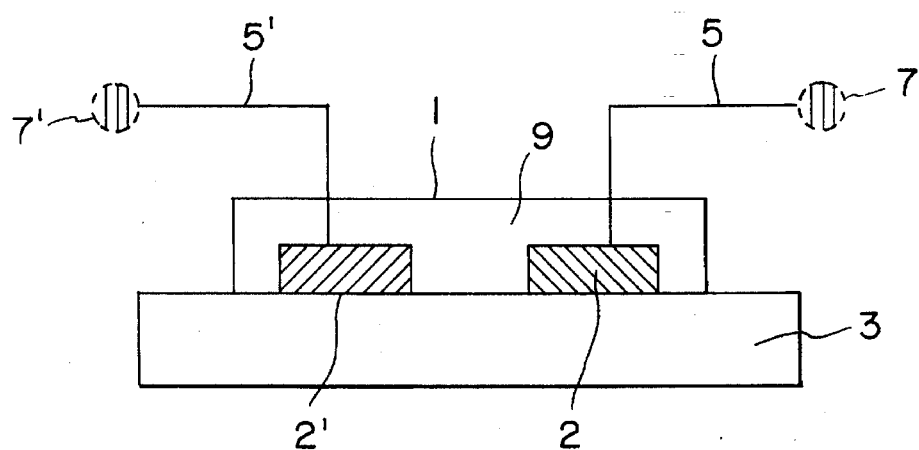
FIG. 1 is a schematic cross-sectional diagram of one embodiment of the invention.

In sensor 1 of FIG. 1, two or more electrical contacts 2, 2' . . . are disposed on an insulating substrate 3, which may consist of silicon, silicon dioxide, alumina, polytetrafluoroethylene, phenolic polymer, melamine polymer, or similar substances. Electrical connections 5, 5' . . . are provided between contacts 2, 2' . . . and external terminals 7, 7' . . . for insertion of sensor 1 into an impedance measuring circuit. Above contacts 2, 2' . . . is a chemiresistive layer 9 comprising a mixture of electrically conductive particles, e.g., of a powder of carbon, copper, silver, gold, platinum, or other suitable metal, and of an elastomer that swells when exposed to the vapor of interest, such as silicone for detecting hexane or polyisobutylene for detecting carbon tetrachloride. The powder may comprise very fine particles, e.g., less than 0.1 micron in size, or intermediate-size particles of 0.1–5 microns, or even coarser particles of 5–300 microns in size.

Figure 2A:
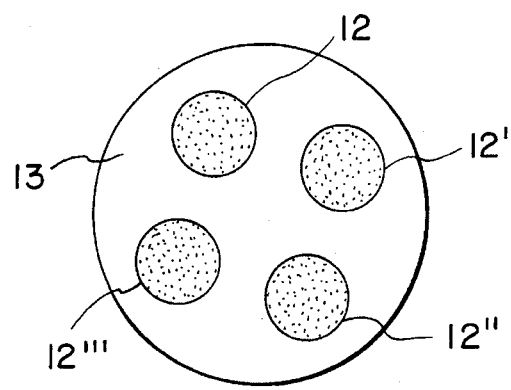
FIG. 2 depicts a variation of the embodiment of FIG. 1.
Figure 2B:
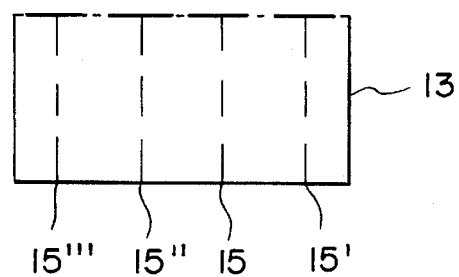
Figure 2C:
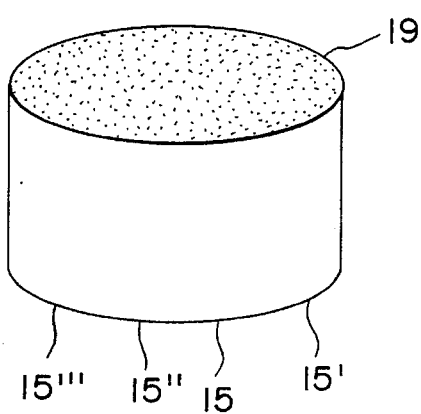

An alternative structure based on the same principle is shown in FIG. 2. FIGS. 2a and 2b are top and side views of a disc-shaped polytetrafluoroethylene substrate 13 in which are embedded four gold-plated pins 15, 15', 15", 15"' covered by four gold-plated pin connectors 12, 12', 12", 12"'. As shown in FIG. 2c, the pin connectors are covered by a carbon-silicone membrane 19, which acts as a chemiresistor when exposed to cyclohexane vapor. Membrane 19 may be formed by spin-coating, spraying, or doctor blading (spreading) an elastomer-carbon mixture in a carrier solvent followed by evaporation of the solvent. Photolithography may be used to define the region occupied by the carbon-silicone material.

Figure 3:
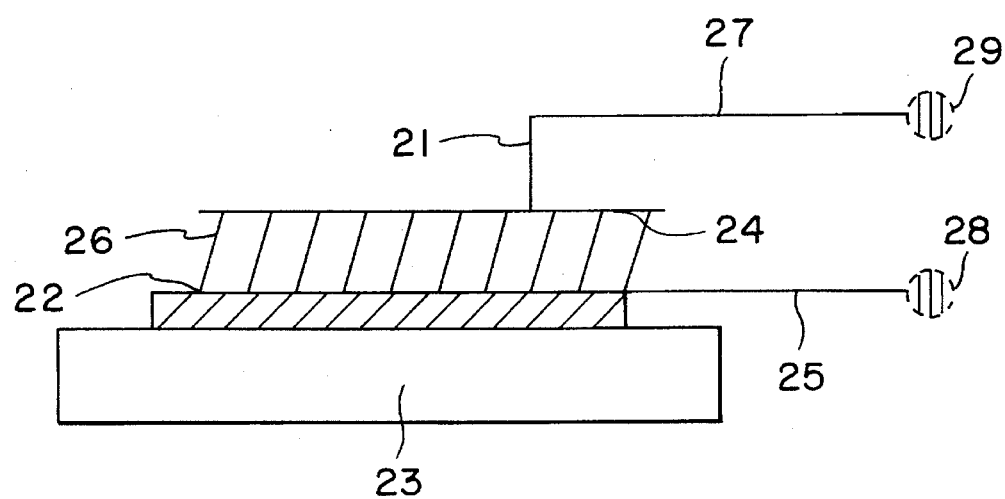
FIG. 3 is a schematic cross-section of one alternative embodiment.

In the alternative embodiment of FIG. 3, a capacitive sensor 21 comprises a lower electrically conductive layer 22 supported on an insulating substrate 23 and separated from an upper conductive layer 24 by an elastomer 26. The upper conductive layer 24 is porous, so that analyte vapor can readily penetrate therethrough into the elastomer layer so as to cause swelling of the elastomer. Such swelling increases the separation between layers 22 and 24, thereby reducing the capacitance and hence increasing the impedance between these layers. Electrical connections 25 and 27 to terminals 28 and 29 permit insertion of sensor 21 into a capacitance- or impedance-measuring circuit.

Figure 4:
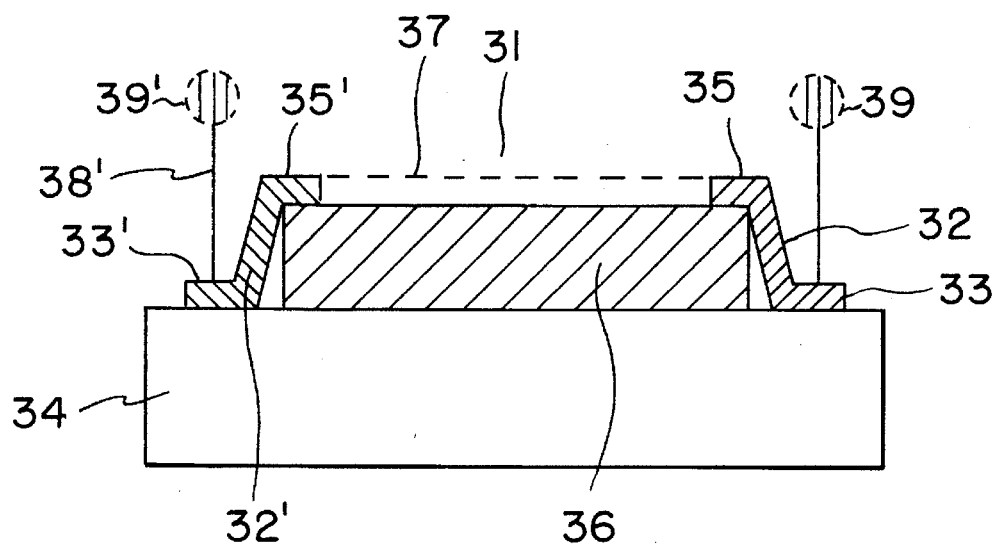
FIG. 4 is a schematic cross-section of another alternative embodiment.

In yet another embodiment, shown in FIG. 4, a sensor 31 comprises two electrical contacts 32, 32' having ends 33, 33' affixed to an insulating support 34 and ends 35, 35' supported by an elastomer 36 and contacting a thin porous or grid-like resistive film 37, which may be a grid-like film of metal, such as gold, silver, copper, or aluminum, about 0.1 micron thick, formed by vacuum evaporation and photolithographic masking or etching techniques. Contacts 33, 33' are connected by electrical leads 38, 38' to terminals 39, 39'. When analyte vapor penetrates through film 37 into elastomer 36, the elastomer swells, thereby causing an increase in the resistance between contacts 32 and 32'.

In FIGS. 1, 2, and 4, the elastomer may be replaced by a polymer that disintegrates upon exposure to an analyte vapor, e.g., polystyrene when exposed to acetone. Here again, the interconnections between the conductive elements weaken upon disintegration of the binding polymer, thereby causing a change in resistance between the contacts 2 and 2' or 12, 12', 12" and 12"', or 32 and 32'.

Figure 5:
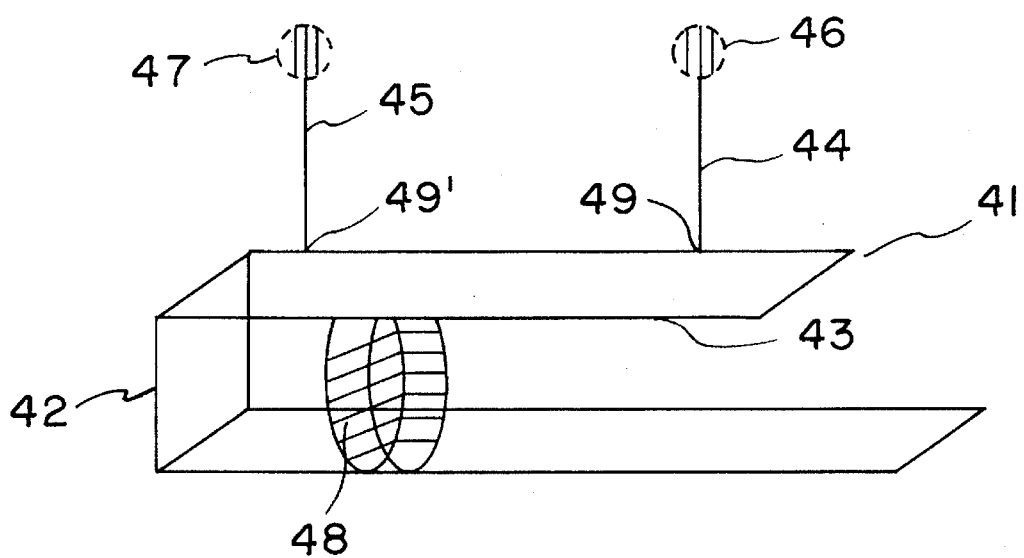
FIG. 5 is a schematic cross-section of yet another embodiment.

In still another embodiment of the invention, shown in FIG. 5, a sensor 41 comprises a U-shaped piezoresistor 42, of which one arm 43 is connected by electrical leads 44 and 45 to terminals 46 and 47. An elastomer 48 exerts pressure against arm 43 at a point that is intermediate between the contacts 49 and 49' (to leads 44 and 45), thereby increasing the piezoresistance of arm 43, especially when the elastomer is caused to swell upon exposure to an analyte vapor. The increased resistance is thus indicative of the presence of analyte vapor.

Figure 6:
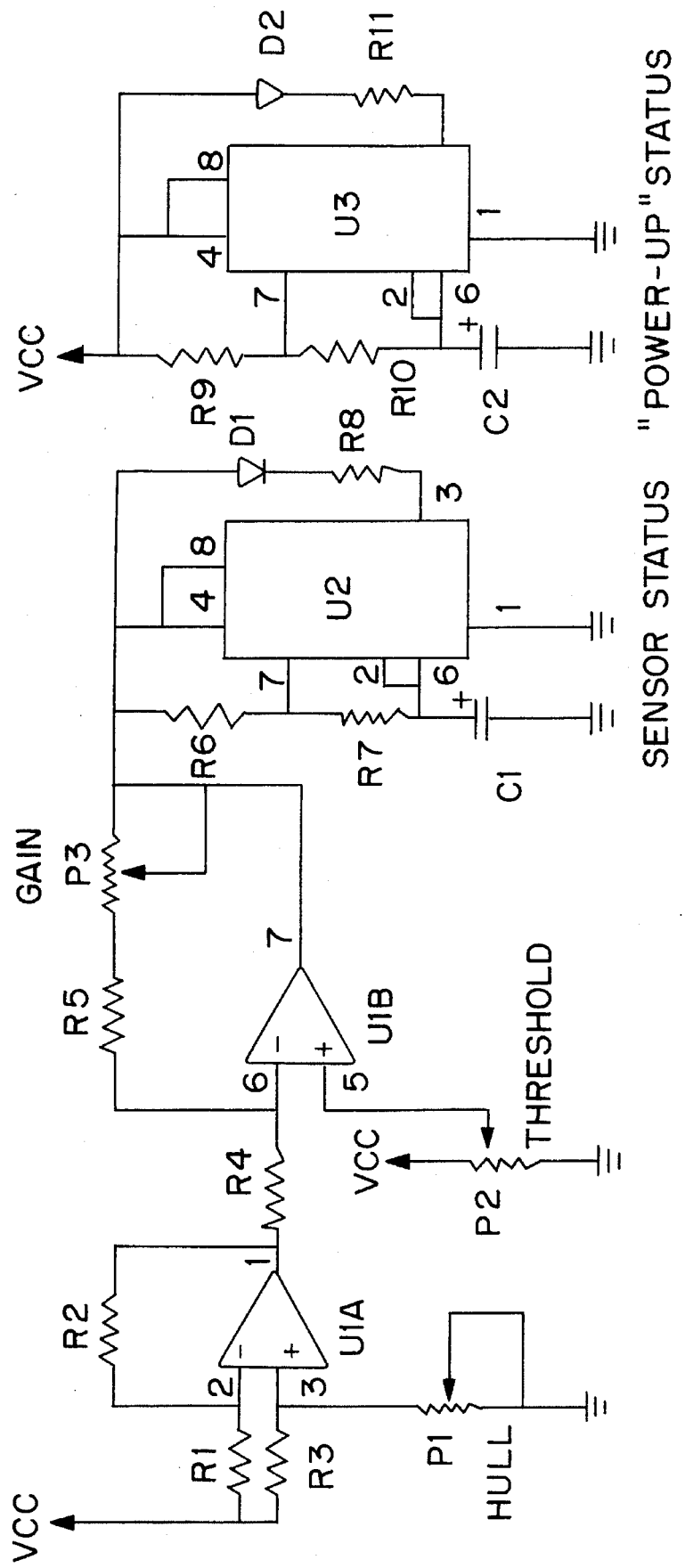
FIG. 6 is a diagram of a circuit operating in conjunction with the sensors of FIGS. 1 through 5.

A circuit for use with the chemiresistive sensors of FIGS. 1, 2 and 4 is shown in FIG. 6. The sensor R1 is in a linear bridge formed with the first operational amplifier U1A. The potentiometer P1 is employed to permit balancing the bridge for sensors which have a base resistance of up to 100 kiloohms. The second operational amplifier U1B is used to control the signal level and the gain by means of the adjustable feedback resistor P3. The output is used to control a low power CMOS (complementary metal oxide semiconductor) version of a timer switch U2 (such as the general purpose timer ICM 7555, Maxim Integrated Products Inc., Sunnyvale, Calif.), making it drive a red warning light-emitting diode (LED) D1 at a fixed frequency when a pre-set signal level is reached. In this circuit, the brightness of the red LED D1 increases with the signal level to a maximum. A standard 9-volt battery powers both the U2 timer and a second timing circuit based on a timer chip U3 which flashes a green LED D2 when the power is on. The duty cycle of the green LED is about 0.1 second on and 10 seconds off. The red alarm LED flashes about once every second for a time interval of 0.1 second. The duty cycles are easily adjustable using resistors R7, R10 and capacitors C1, C2 to minimize power consumption through a choice of passive components.

To minimize the current requirement, low power chips and selected high resistance values may be used for the bridge circuit. The precision low-power dual operational amplifier chip OP290 (Precision Monolithics, Santa Clara, Calif.), for example, has a quiescent current of 5 μA. Using the OP290 amplifier and ICM 7555 timers to produce a current drain of less than 0.1 mA at 9 volts, a lithium battery weighing only 5 grams should suffice for more than 5000 hours (500 mAH) in use or for operating the alarm (a 7-mA LED) for 70 hours. Since the device need only be powered when in use, the battery lifetime could be measured in years.

Among the polymers that may be used in the embodiments of FIGS. 1 through 5 are EP (ethylene propylene polymer), SBR (styrene butadiene resin), VMQ (silicone), FVMQ (fluorosilicone), BR (butyl rubber or polybutadiene), II (isobutylene isoprene polymer), CP (chloroprene polymer), FKM (fluorocarbon polymer), and ACM (polyacrylate). Except for ACM, all these polymers exhibit little or no sensitivity to water. Insensitivity to water is desirable to minimize interference from ambient water vapor. Table 1 shows how these polymers are affected by various chemical substances.

TABLE 1

Dimensional Changes in Various Polymers Upon Exposure to Various Chemical Substances.
S = swelling; N = no change; C = contraction

| CHEMICAL SUBSTANCE | POLYMER: | | | | | | | | |
|---|---|---|---|---|---|---|---|---|---|
| | EP | SBR | VMQ | FVMQ | BR | II | CP | FKM | ACM |
| CYCLOHEXANE | S | S | S | | S | S | | | |
| HEXANE | S | S | S | | S | S | | | |
| STYRENE | S | S | S | | S | S | | | |
| GASOLINE | S | S | S | | S | S | | | |
| KEROSENE | S | S | S | | S | S | | | |
| CARBON TETRACHLORIDE | S | S | S | | S | S | | | |
| ACETONE | N | N | N | S | S | C | | S | S |
| WATER | N | N | N | | N | N | | | S |
| ISOPROPANOL | N | N | N | N | N | N | N | N | S |
| METHANOL | N | N | N | N | N | N | N | N | S |
| TRICHLOROETHYLENE | S | S | | | S | S | | | |
| TRICHLOROETHANE | S | S | | | S | S | | | |
| TOLUENE | S | S | | | S | S | | | |

The characteristics of some of the sensors according to one of the afore-described embodiments are illustrated in the following examples:

EXAMPLE 1

Figure 7:
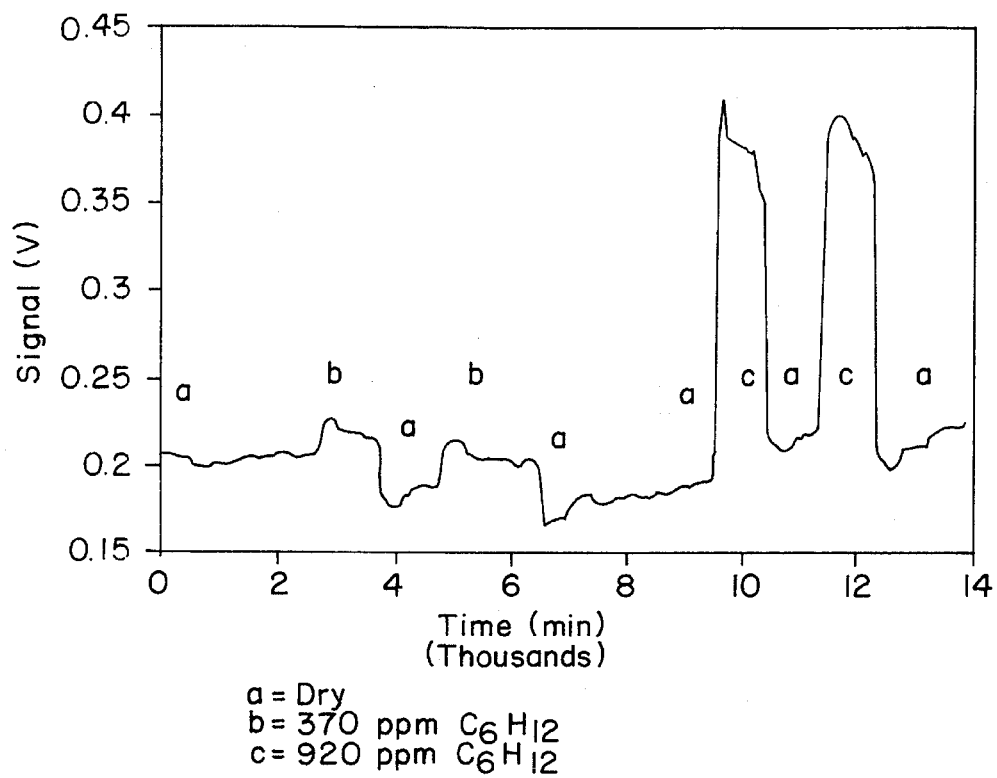
FIG. 7 shows test results obtained with a typical embodiment based on FIG. 1.

Sensors were made by spraying a mixture of 75% Dow Corning 92-009 Silicone Dispersion and 25% carbon (by weight) directly onto small cylindrical Teflon [polytetrafluoroethylene] substrates (1 cm in diameter) that had gold plated contacts (0.15 cm in diameter) on the top surface, according to the design of FIG. 2. The contacts were connected to pins extending out of the base of the device. The carbon used was a Darco G-60 (comprising particles 20–300 microns in size, supplied by Frederick G. Smith Co., Columbus, Ohio) treated with a silanizing agent (Glassclad 6C, supplied by Emulsitone Co., Whippany, N.J.) to produce a hydrophobic surface. The goal of the treatment was to produce a more uniform mixture of carbon and silicone by preventing the clumping of carbon granules. FIG. 7 shows the response of the sensor to increasing concentrations of cyclohexane in air.

EXAMPLE 2

Figure 8C:
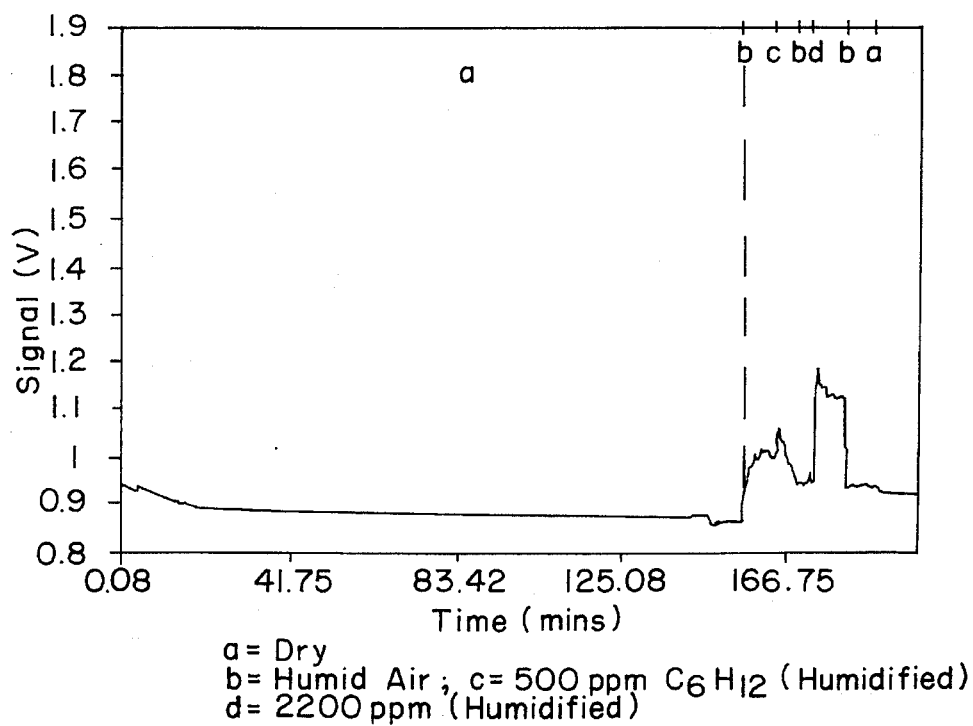
FIG. 8 shows test results obtained with an alternative sensor based on FIG. 1.
Figure 8A:
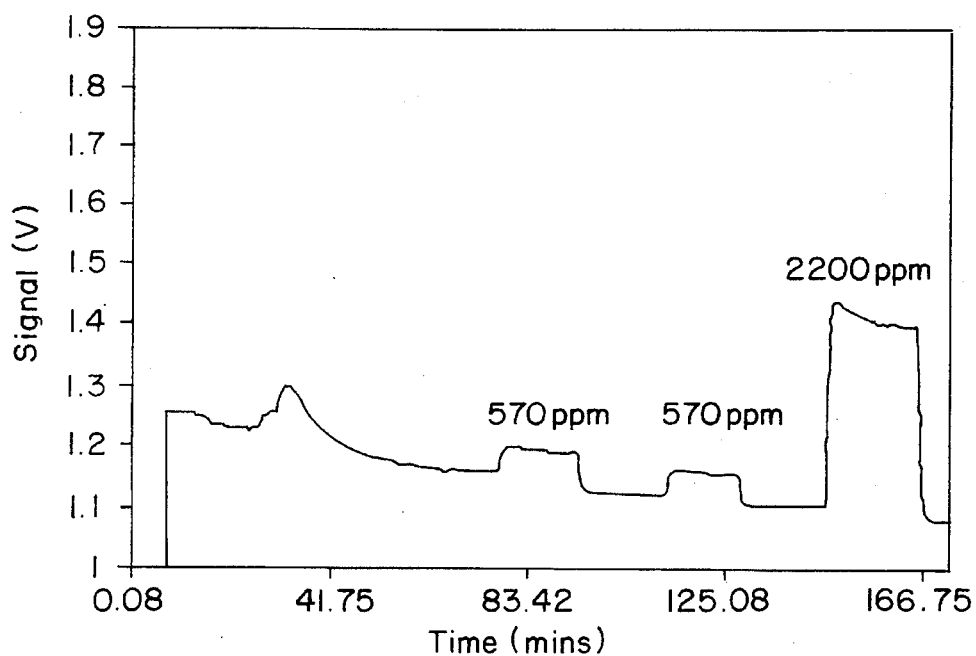
Figure 8B:
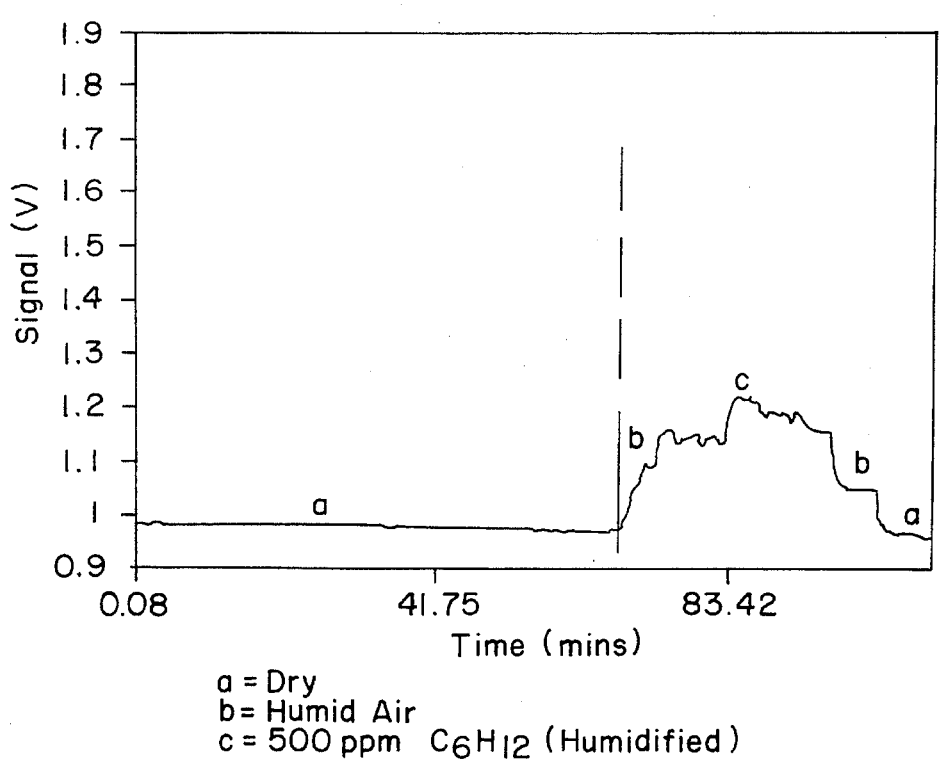

A miniaturized sensor was made by applying two 0.1"× 0.1" contact pads of etched copper, spaced 0.1" apart, on a printed circuit board. A 0.1"-wide strip of a cured film of a 25% Darco/75% silicone mixture, several thousandths of an inch thick, was placed over the contact pads and the space between the pads and joined to the contact pads with silver-epoxy paint. The sensor was then challenged by cyclohexane concentrations of 570 ppm (parts per million by volume) and 2200 ppm first in dry air (FIG. 8a) and subsequently in humidified air at 95% relative humidity (FIGS. 8b and 8c). It is clear from FIGS. 8a, b, and c that the sensor responds well to different concentrations of cyclohexane. However, it also appears from FIGS. 8b and c that humidity alone results in a signal that is equivalent to about 1,000 ppm of cyclohexane in dry air.

In order to compensate for the effects of humidity and possibly also of temperature, it is preferable to have two substantially identical sensors in a respirator cartridge—a first sensor placed in front of the deepest relatively unused portion of the filter bed (which may comprise about 10% of the entire bed) and a second sensor placed near the very end of the filter bed. Except for the small separation by said unused bed portion, the two sensors are situated as closely to each other as practicable, so that the second sensor is exposed to approximately the same humidity and temperature as the first sensor and can therefore serve to compensate for the effects of these variables. Any significant differences between the signals from the first and second sensors are then attributable to the penetration of analyte vapor to the first sensor.

EXAMPLE 3

Figure 9:
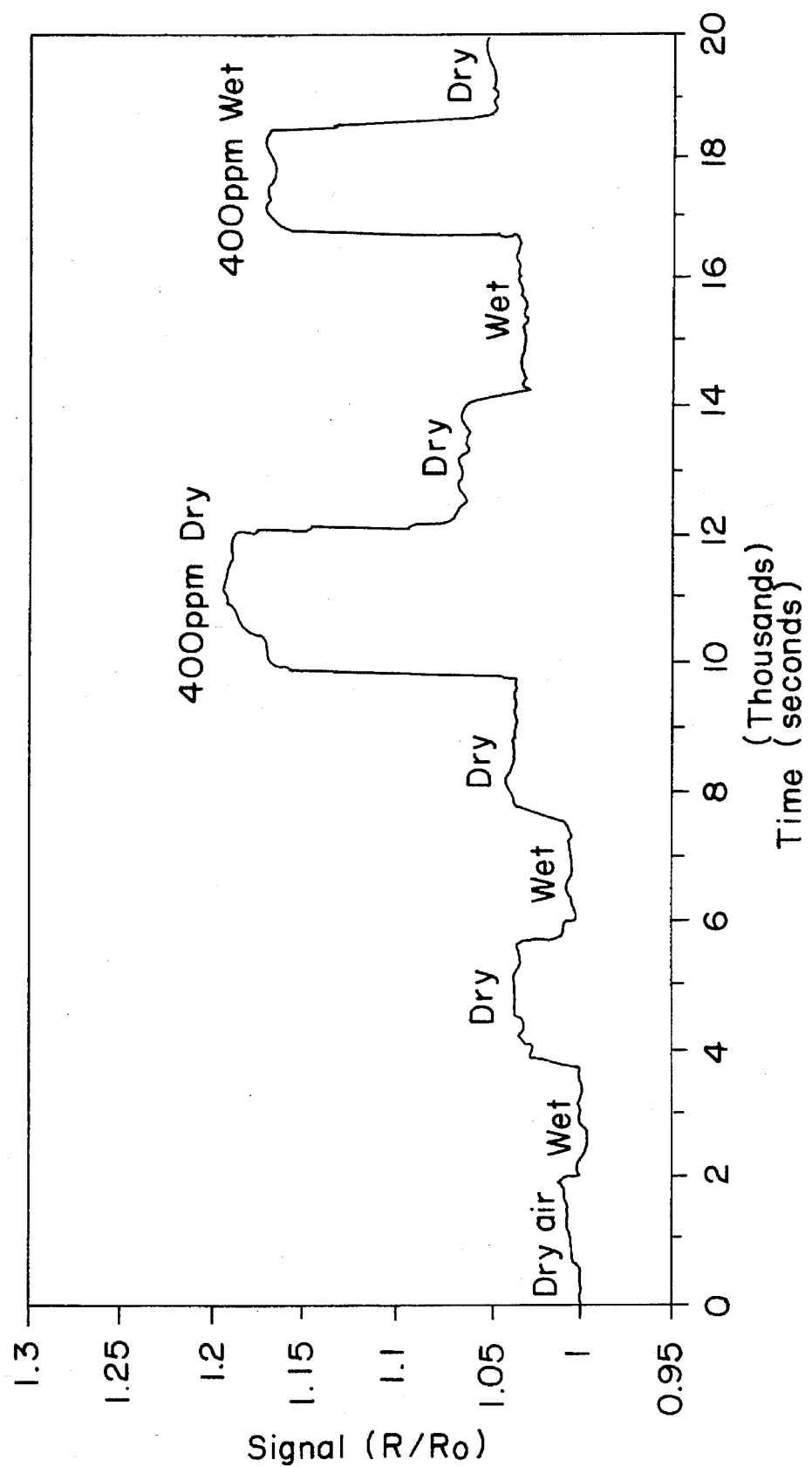
FIG. 9 shows test results obtained with yet another variation of the embodiment of FIG. 1.

Two sensors were made in a similar way as in Example 1, except that the Darco G-60 carbon particles were not silanized. The sensors were inserted in a bridge circuit, with both sensors exposed to the same relative humidity conditions (70% and 0.5% relative humidity, denoted as "wet" and "dry," respectively). Only one of these sensors was exposed to cyclohexane vapor. The effect of the compensation is shown in FIG. 9, in which the relative value of the measured sensor resistance is used as the sensor signal. The response to 400 ppm of cyclohexane can be seen to be independent of relative humidity within experimental error.

Alternatively, in some cases it may be preferable to cover a sensor with a membrane that is permeable to water vapor but not to the compound to be detected, or vice versa, and thereby provide sufficient information to determine the signal due to the compound exclusive of the effect of moisture. For instance, using a hydrophobic polytetrafluoroethylene membrane to cover a sensor, the sensor could be immersed in a liquid containing water and gasoline and successfully detect the hydrocarbons in the presence of water.

There will now be obvious to those skilled in the art many modifications and variations of the afore-disclosed embodiments which, however, shall remain within the scope of the invention if defined by the following claims.

We claim:

1. Apparatus for indicating the end of service life of a filter cartridge for removing vapors of a chemical species from respired air, including a sensor that comprises:

a polymer whose physical structure changes upon exposure to said chemical species, discrete electrically conductive elements at least partly separated by said polymer, and an impedance-measuring means for measuring the impedance between two of said conductive elements, wherein a change in said polymer's physical structure upon exposure to said chemical species results in an increase in the impedance between said two conductive elements, and wherein the change in physical structure consists of partial or complete disintegration of said polymer.

2. Apparatus for indicating the end of service life of a filter cartridge for removing vapors of a chemical species from respired air, including a sensor that comprises:

a polymer whose physical structure changes upon exposure to said chemical species, electrically conductive elements interspersed within and at least partly separated by said polymer, and an impedance-measuring means for measuring the impedance between two of said conductive elements, wherein a change in said polymer's physical structure upon exposure to said chemical species results in a change in the impedance between said two conductive elements, and wherein said conductive elements comprise two spaced electrical contacts on an electrically insulating substrate, said contacts being electrically connected to, and bridged by, a layer of said polymer admixed with a multiplicity of said conductive elements.

3. The apparatus of claim 2, wherein said layer is mechanically bonded to each of said contacts.

4. The apparatus of claim 3, wherein said layer is joined to said contacts by an electrically conductive adhesive.

5. The apparatus of claim 4, wherein said adhesive is a mixture of silver particles and epoxy resin.

6. The apparatus of claim 2, wherein said layer is in the form of an adherent coating covering parts or all of said contacts and said substrate.

7. The apparatus of claim 2, wherein said insulating substrate comprises an inorganic substance.

8. The apparatus of claim 7, wherein said inorganic substance comprises silicon, silicon dioxide or aluminum oxide.

9. The apparatus of claim 2, wherein said insulating substrate comprises organic material.

10. The apparatus of claim 9, wherein said organic material comprises polytetrafluoroethylene, phenolic polymer or melamine polymer.

11. Apparatus for indicating the end of service life of a filter cartridge for removing vapors of a chemical species from respired air, including a sensor that comprises:

a polymer whose physical structure changes upon exposure to said chemical species, electrically conductive elements at least partly separated by said polymer, and an impedance-measuring means for measuring the impedance between two of said conductive elements, wherein a change in said polymer's physical structure upon exposure to said chemical species results in an increase in the impedance between said two conductive elements and wherein said conductive elements form two substantially parallel layers separated by said polymer, one of said layers having a vapor-permeable structure permitting permeation of vapor to said polymer.

12. Apparatus for indicating the end of service life of a filter cartridge for removing vapors of a chemical species from respired air, including a sensor that comprises:

a polymer whose physical structure changes upon exposure to said chemical species, electrically conductive elements at least partly separated by said polymer, and an impedance-measuring means for measuring the impedance between two of said conductive elements, wherein a change in said polymer's physical structure upon exposure to said chemical species results in a change in the impedance between said two conductive elements, and wherein said conductive elements comprise two spaced electrical contacts on an electrically insulating base, said contacts being bridged by a vapor-permeable conductor that is separated from said base by said polymer.

13. Apparatus for indicating the end of service life of a filter cartridge for removing vapors of a chemical species from respired air, including a sensor that comprises:

a polymer whose physical structure changes upon exposure to said chemical species from said air, discrete electrically conductive elements at least partly separated by said polymer, and an impedance-measuring means for measuring the impedance between two of said conductive elements, wherein a change in said polymer's physical structure upon exposure to said chemical species results in a change in the impedance between said two conductive elements, wherein said polymer appertains to the family of polymers that consists of ethylene propylene polymer, styrene butadiene resin, polybutadiene, isobutylene-isoprene polymer, chloroprene polymer, fluorocarbon polymer, and polyacrylate.

14. Apparatus for indicating the end of service life of a filter cartridge for removing vapors of a chemical species from respired air, including a sensor that comprises:

a polymer whose physical structure changes upon exposure to said chemical species from said air, discrete electrically conductive elements at least partly separated by said polymer, and an impedance-measuring means for measuring the impedance between two of said conductive elements, wherein a change in said polymer's physical structure upon exposure to said chemical species results in a change in the impedance between said two conductive elements, wherein said sensor is a first sensor and further comprising a second sensor similar to said first sensor exposed to substantially the same temperatures and humidities, only one of the two sensors being accessible to vapor of said chemical species, wherein said polymer in one of said sensors is covered by a selectively permeable membrane, said membrane being permeable to water vapor but not to said chemical species.

15. Apparatus for indicating the end of service life of a filter cartridge for removing vapors of a chemical species from respired air, including a sensor that comprises:

a polymer whose physical structure changes upon exposure to said chemical species from said air, discrete electrically conductive elements at least partly separated by said polymer, and an impedance-measuring means for measuring the impedance between two of said conductive elements, wherein a change in said polymer's physical structure upon exposure to said chemical species results in a change in the impedance between said two conductive elements, wherein said polymer is covered by a selectively permeable membrane that is permeable to said chemical species but not to water vapor, and wherein said membrane comprises a fluorinated polymer.

16. The apparatus of claim 15, wherein said fluorinated polymer comprises polytetrafluoroethylene.

17. A method of producing a sensor for detecting vapors of a chemical species which comprises bringing a polymer whose physical structure changes upon exposure to said chemical species into firm adhesive and electrical contact with an electrically conductive element, wherein said conductive element is affixed onto an electrically insulating base and coated with a layer of said polymer.

18. The method of claim 17, which further comprises admixing electrically conductive particles with said polymer prior to said coating step.

19. The method of claim 18, wherein said polymer is a silicone or polyisobutylene and said particles comprise carbon.

20. The method of claim 18, wherein the boundaries of said layer are defined by a photolithographic technique.

21. The method of claim 17, wherein said coating step comprises spraying, spreading with a doctor blade, or spin-coating said polymer or a mixture of said polymer with electrically conductive particles in a carrier solvent over said conductive element and allowing the solvent to evaporate.

22. The method of claim 21, wherein said mixture comprises carbon particles and silicone.

23. The method of claim 22, further comprising the step of silanizing the carbon particles before admixing them with the silicone.

24. The method of claim 17 comprising a further step of affixing over said polymer layer a vapor-permeable electrically conductive layer.

25. The method of claim 24, wherein said vapor-permeable electrically conductive layer is applied to said polymer layer by vacuum evaporation.

26. The method of claim 25, wherein said vacuum evaporation step utilizes a photolithographic masking or etching technique.

* * * * *